(12) United States Patent
Simon et al.

(10) Patent No.: US 6,225,484 B1
(45) Date of Patent: May 1, 2001

(54) PROCESS FOR THE PREPARATION OF BETA-METHOXYACRYLATES

(75) Inventors: Werner Simon, Hueffelsheim; Thomas Petry, Mainz, both of (DE)

(73) Assignee: American Cyanamid Co., Madison, NJ (US)

( * ) Notice: Subject to any disclaimer, the term of this patent is extended or adjusted under 35 U.S.C. 154(b) by 0 days.

(21) Appl. No.: 09/373,263

(22) Filed: Aug. 12, 1999

(51) Int. Cl.⁷ .............................. C07C 51/00; C07C 67/00
(52) U.S. Cl. .................. 554/124; 554/68; 560/55; 560/56
(58) Field of Search .................. 554/124, 68; 560/55, 560/56

(56) References Cited

FOREIGN PATENT DOCUMENTS

99/12892    3/1999    (WO).

OTHER PUBLICATIONS

Martin et al, Tetrahedron Letters vol. 34, No. 32 pp. 5151–5154, entire article, 1993.*
Martin et al, Tetrahedron Letters, vol. 34, No. 32, pp. 5151–5154 (1993).

* cited by examiner

Primary Examiner—Samuel Barts
Assistant Examiner—Diedra Faulkner

(74) Attorney, Agent, or Firm—Barbara L. Renda; Barbara V. Maurer

(57) ABSTRACT

The invention relates to an improved process for the preparation of a compound of formula I

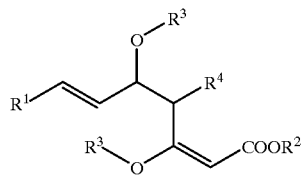

(I)

wherein $R^1$ represents an optionally substituted aryl group,
$R^2$ represents an optionally substituted alkyl group, and
$R^3$ and $R^4$ each individually represent an alkyl group;

which comprises heating a mixture of a compound of formula II

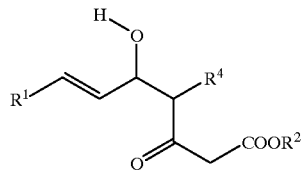

(II)

an alcohol, a tri-alkoxymethane, an acid and, optionally, an inert diluent.

13 Claims, No Drawings

PROCESS FOR THE PREPARATION OF BETA-METHOXYACRYLATES

BACKGROUND OF THE INVENTION

The invention relates to an improved process for the preparation of 7-aryl-3,5-dialkoxy-4-alkyl-hepta-2,6-dienoic acid alkyl ester which comprises reacting the corresponding 3-aryl-propenal with a 3-oxo-alkanoic acid alkyl ester to afford a 7-aryl-3,5-dihydroxy-4-alkyl-hepta-2,6-dienoic acid alkyl ester which is then subsequently alkylated.

7-aryl-3,5-dialkoxy-4-alkyl-hepta-2,6-dienoic acid alkyl esters are useful as intermediates for the preparation of a variety of beta-methoxyacrylates which are useful as fungicides. In particular, they are key intermediates in the preparation of myxothiazole and oudemansins which are described, for example, in Martin et al., Tetrahedron Letters, 32, 5151, 1993.

7-aryl-3,5-dialkoxy-4-alkyl-hepta-2,6-dienoic acid alkyl esters are generally disclosed in WO 99/12892 but there is no specific disclosure of their preparation.

Martin et al., Tetrahedron Letters, 34, 32, 5151, 1993 disclose a method for the preparation of myxothiazole which comprises reacting 3-phenyl-propenal with 3-oxo-pentanoic acid methyl ester followed by three methylation steps to yield 7-phenyl-3,5-dimethoxy-4-alkyl-hepta-2,6-dienoic acid methyl ester as an intermediate for myxothiazole. This process requires many steps to achieve an overall yield of the desired 7-aryl-3,5-dialkoxy-4-methyl-hepta-2,6-dienoic acid alkyl ester of less than 20%.

The novel process of the present invention has been found to be advantageous in producing 7-aryl-3,5-dialkoxy-4-alkyl-hepta-2,6-dienoic acid alkyl esters with high overall yields in only one or two steps.

It is an object of the present invention to provide an efficient and improved process for the preparation of 7-aryl-3,5-dialkoxy-4-alkyl-hepta-2,6-dienoic acid alkyl esters of formula I.

Other objects and advantages of the present invention will be apparent to those skilled in the art from the following description and the appended claims.

SUMMARY OF THE INVENTION

The compounds of formula I

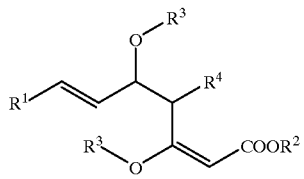

(I)

wherein $R^1$ represents an optionally substituted aryl group, $R^2$ represents an optionally substituted alkyl group, and $R^3$ and $R^4$ each individually represent an alkyl group;

are obtained in high overall yields by an improved process which comprises heating of a mixture which consists essentially of (i) a compound of formula II

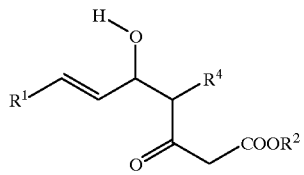

(II)

wherein $R^1$, $R^2$ and $R^4$ are as hereinbefore defined, (ii) an alcohol of formula III, $R^3$—OH   (III)

wherein $R^3$ is as hereinbefore defined, (iii) a tri-alkoxymethane of formula IV, $CH(OR^3)_3$   (IV)

wherein $R^3$ is as hereinbefore defined, and (iv) an acid, and, optionally, an inert diluent.

DETAILED DESCRIPTION OF THE PREFERRED EMBODIMENTS

The instant invention relates to an improved process for the preparation of the compounds of formula I which comprises by heating a mixture consisting essentially of a compound of formula II, an alcohol of formula III, a tri-alkoxymethane of formula IV, an acid, and, optionally, an inert diluent. The compounds of formula II can be obtained by reacting a 3-aryl-propenal with a 3-oxo-alkanoic acid alkyl ester in the presence of a strong base and an inert diluent.

The advantage of the improved process is that the compound of formula I is obtained in high yields and high purity by a one or two step synthesis.

In general terms, unless otherwise stated herein, the term "alkyl" as used herein with respect to a radical or moiety refers to a straight or branched chain radical or moiety. As a rule, such radicals have up to 10, in particular, up to 6, carbon atoms. Preferably an alkyl moiety has from 1 to 6 carbon atoms, and more preferably, from 1 to 3 carbon atoms. A particularly preferred alkyl moiety is the methyl group or ethyl group being optionally substituted by one or more halogen atoms.

In general terms, unless otherwise stated herein, the term "aryl" as used herein with respect to a radical or moiety refers to an aryl group having 6, 10 or 14 carbon atoms, and preferably, 6 or 10 carbon atoms. A particularly preferred aryl moiety is the phenyl group being optionally substituted by one or more halogen atoms, nitro, cyano, alkyl, preferably, $C_{1-6}$ alkyl, haloalkyl, preferably, $C_{1-6}$ haloalkyl, alkoxy, preferably $C_{1-6}$ alkoxy, alkoxyiminoalkyl, preferably 1-($C_{1-6}$ alkoximino) $C_{2-6}$ alkyl.

Suitable alcohols of formula IIIl for use in the present invention are aliphatic alcohols having 1 to 10 carbon atoms, and preferably 1 to 4 carbon atoms, most preferably primary alcohols, in particular methanol or ethanol.

Suitable tri-alkoxymethanes of formula IV are tri-alkoxymethanes having 4 to 13 carbon atoms, preferably 4 to 10 carbon atoms, in particular, trimethoxymethane or triethoxymethane.

Suitable acids for use in the present invention are weak acids, preferably optionally substituted alkylsulfonic acids, arylsulfonic acids, benzoic acids or alkanoic acids, and most preferably, substituted arylsulfonic acids, such as p-toluenesulfonic acid.

Suitable bases for use in the present invention are strong bases, preferably alkali metal hydrides, alkali metal alkanes and alkali metal dialkylamides or mixtures thereof, most preferred being sodium hydride and/or butyl lithium.

Suitable inert diluents are those selected from the group consisting of cyclic ethers, aliphatic ethers, aliphatic hydrocarbons, aromatic hydrocarbons, dimethylsulfone or N,N-dimethylformamide. Most preferred are cyclic ethers such as tetrahydrofuran.

A preferred embodiment of the present invention is a process wherein:

the reaction mixture is heated to temperatures from about 20 to 100° C.; preferably from about 50° C. to 80° C., in particular, from about 60° C. to 70° C.; and most preferably to about 65° C.;

the reaction is carried out at atmospheric pressure;

the reaction mixture consists of a compound of formula II, a primary alcohol, a trialkoxymethane and catalytic amounts of an organic acid, preferably p-toluenesulfonic acid; in a particularly preferred embodiment the mixture consists of 1 mole of a compound of formula II, 20 to 200 moles, in particular 40 to 150 moles, most preferably about 100 moles of a primary alcohol, 5 to 50 moles, in particular, 15 to 40 moles, most preferably about 25 moles of a tri-alkoxymethane and 0.01 to 0.1 moles, preferably 0.02 to 0.08 moles of an organic acid;

$R^1$ represents an aryl group being optionally substituted by one or more halogen atoms, optionally substituted alkyl groups or alkoxy groups, in particular wherein $R^1$ represents a phenyl group;

$R^2$ represents a $C_{1-4}$ alkyl group being optionally substituted by one or more halogen atoms, in particular, wherein $R^2$ represents a methyl or ethyl group;

$R^3$ represents a $C_{1-4}$ alkyl group, in particular, wherein $R^3$ represents a methyl or ethyl group;

$R^4$ represents a $C_{1-4}$ alkyl group, in particular, wherein $R^4$ represents a methyl group.

In a preferred embodiment of the invention, the preparation of a compound of formula I is carried out in a two-step synthesis comprising the steps of a) reaction of a 3-aryl-propenal with a the dianion of an 3-oxo-alkanoic acid alkyl ester of formula V

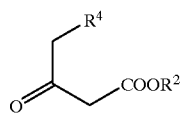

(V)

which is generated in situ with the aid of 1.8 to 2.6 equivalents of a strong base, preferably sodium hydride and/or butyl lithium in an inert diluent, subsequently treating the resulting mixture with a dilute acid, and b) treating the resulting 7-aryl-3,5-dihydroxy-4-alkyl-hepta-2,6-dienoic acid alkyl esters with an alcohol, a tri-alkoxymethane and an acid, optionally, in an inert diluent.

Another preferred embodiment of the present invention is a process wherein in step a)

the reaction is carried out at temperatures between −5 and 30° C.; preferably between −3° C. and 20° C., in particular at about 0° C.;

the reaction is carried out at atmospheric pressure;

the reaction comprises treating a compound of formula V with 1.8 to 2.6 equivalents of a strong base, preferably a mixture of sodium hydride and butyl lithium in an inert diluent, subsequently treating the resulting dianion with a vinylformyl compound of formula VI, and finally treating the addition product with an acid, preferably a mineral acid, in particular hydrochloric acid.

$R^1$ represents an aryl group being optionally substituted by one or more halogen atoms, optionally substituted alkyl groups or alkoxy groups, in particular, wherein $R^1$ represents a phenyl group $R^2$ represents a $C_{1-4}$ alkyl group being optionally substituted by one or more halogen atoms, in particular, wherein $R^2$ represents a methyl or ethyl group;

$R^3$ represents a $C_{1-4}$ alkyl group, in particular, wherein $R^3$ represents a methyl or ethyl group; and $R^4$ represents a $C_{1-4}$ alkyl group, in particular, wherein $R^4$ represents a methyl group.

The crude product obtained can be purified according to standard methods, for example, by distillation, or chromatographic methods. However, the crude product obtained according to the process of this invention is usually sufficiently pure to be used as intermediate without further purification.

In a particularly preferred embodiment of the process according to this invention, the compound of formula II is 7-phenyl-3,5-dihydroxy-4-methyl-hepta-2,6-dienoic acid methyl ester. The compound of formula II can be prepared by a reaction between 3-phenyl-propenal and the dianion of 3-oxo-pentanoic acid methyl ester generated with the aid of a strong base, preferably sodium hydride and/or butyl lithium, at a temperature of about 0° C.

In another particularly preferred embodiment of the process according to this invention a mixture of the compound of formula II, in particular, 7-phenyl-3,5-dihydroxy-4-methyl-hepta-2,6-dienoic acid methyl ester, an alcohol, preferably methanol, a tri-alkoxymethane, preferably trimethoxymethane, and a catalytic amount of an acid, preferably p-toluenesulfonic acid is heated to about 65° C. The compound of formula I, in particular 7-phenyl-3,5-dimethoxy-4-methyl-hepta-2,6-dienoic acid methyl ester, is obtained and purified by standard methods, for instance, by chromatographic methods.

In order to facilitate a further understanding of the invention, the following illustrative examples are presented. The invention is not limited to the specific embodiments described or illustrated, but encompasses the full scope of the appended claims.

Example 1

Preparation of 7-phenyl-3,5-dihydroxy-4-methyl-hepta-2,6-dienoic Acid Methyl Ester 13.0 g 3-Oxo-pentanoic acid methyl ester were added to a suspension of 4.4 g of sodium hydride in 250 ml tetrahydrofurane at 0° C. within over a period of about ten minutes and the reaction mixture is stirred for an additional ten minutes. Subsequently, 42.4 ml of butyl lithium in n-hexane (2.5 molar) were added at 0° C. over a period of fifteen minutes and the reaction mixture was stirred for ten minutes. 14.5 g of 3-phenyl-propenal is then added. After stirring, the reaction mixture for ten minutes, 20 ml concentrated hydrochloric acid, 50 ml water and 350 ml diethylether were added successively. The organic phase was separated off, washed and dried. The solvent was removed in vacuo to yield 30 g of an oil having a refraction index of 1.547 at 20° C. The oil was used for the preparation of 7-phenyl-3,5- dimethoxy-4-methyl-hepta-2,6-dienoic acid methyl esters without further purification.

EXAMPLE 2

Preparation of 7-phenyl-3,5-dimethoxy-4-methyl-hepta-2,6-dienoic Acid Methyl Esters A mixture of 10.4 g of 7-phenyl-3,5-dihydroxy-4-methyl-hepta-2,6-dienoic acid methyl esters obtained in Example 1, 100 ml trimethoxymethane, 100 ml methanol and 0.25 g p-toluenesulfonic acid was stirred at 65° C. for 15 hours. Subsequently the reaction mixture was concentrated in vacuo and then applied onto a flash chromatography column. The column is consecutively eluted with petrol ether/diethylether (93:7 v/v) to yield 7.0 g of a yellow oil having a refraction index of 1.5498. at 20 ° C. Refraction indexes of diastereoisomers are 1.5385 and 1.5531 at 20° C.

What is claimed is:

1. A process for the preparation of a compound of formula I

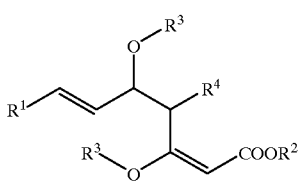

(I)

wherein
$R^1$ represents an optionally substituted aryl group,
$R^2$ represents an optionally substituted alkyl group, and
$R^3$ and $R^4$ each individually represent an alkyl group;
which comprises heating a mixture consisting essentially of
(i) a compound of formula II

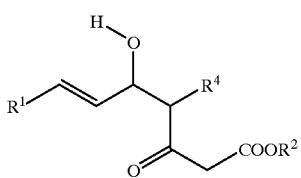

(II)

wherein $R^1$, $R^2$ and $R^4$ are as hereinbefore defined,
(ii) an alcohol of formula III,

(III)

wherein $R^3$ is as hereinbefore defined,
(iii) a tri-alkoxymethane of formula IV,

(IV)

wherein $R^3$ is as hereinbefore defined,
(iv) an acid and optionally an inert diluent.

2. A process according to claim 1, wherein the reaction is carried out at a temperature from 40° C. to 100° C.

3. A process according to claim 1, wherein the alcohol of formula III is methanol or ethanol.

4. A process according to claim 1, wherein the tri-alkoxymethane of formula IV is trimethoxymethane or triethoxymethane.

5. A process according to claim 1, wherein the acid is selected from the group consisting of optionally substituted alkylsulfonic acids, arylsulfonic acids, benzoic acids and alkanoic acids.

6. A process according to claim 5, wherein the organic acid is p-toluenesulfonic acid.

7. A process according to claim 1, wherein the organic acid is used in catalytic amounts.

8. A process according to claim 1, wherein the diluent is selected from the group consisting of benzene, toluene, N,N-dimethylformamide, tetrahydrofurane and dimethylsulfoxide.

9. A process according to claim 1, wherein $R^1$ represents a phenyl group being optionally substituted by one or more halogen atoms, nitro, cyano, alkyl or alkoxy groups.

10. A process according to claim 1, wherein $R^2$ represents a $C_{1-4}$ alkyl group being optionally substituted by one or more halogen atoms.

11. A process according to claim 10, wherein $R^2$ represents a methyl group or ethyl group.

12. A process according to claim 1, which further comprises the steps of (a) treating one equivalent of an 3-oxo-ester of formula V,

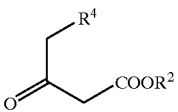

(V)

with 1.8 to 2.6 equivalents of a strong base in the presence of an inert diluent;

(b) treating the resulting reaction mixture with about one equivalent of a vinyl-formyl compound of formula VI,

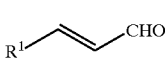

(VI)

to obtain a reaction mixture comprising the compound of formula I, (c) treating the reaction mixture with an acid and concentrating the resulting mixture, and (d) heating the residue with a mixture essentially consisting of a primary alcohol, a tri-n-alkoxymethane, an acid, and, optionally, an inert diluent.

13. A process according to claim 12, wherein the strong base of step (a) is selected from the group consisting of alkali metal hydrides, alkali metal alkanes, alkali metal dialkylamides and mixtures thereof.

* * * * *